US008092433B2

(12) United States Patent
Hamdy (10) Patent No.: US 8,092,433 B2
(45) Date of Patent: Jan. 10, 2012

(54) DYSPHAGIA RECOVERY BY ELECTRICAL STIMULATION

(75) Inventor: Shaheen Hamdy, Wilmslow (GB)

(73) Assignee: Phagenesis Limited, Ledbury (GB)

( * ) Notice: Subject to any disclaimer, the term of this patent is extended or adjusted under 35 U.S.C. 154(b) by 0 days.

(21) Appl. No.: 11/661,420

(22) PCT Filed: Aug. 23, 2005

(86) PCT No.: PCT/GB2005/003289
§ 371 (c)(1),
(2), (4) Date: Feb. 28, 2007

(87) PCT Pub. No.: WO2006/024825
PCT Pub. Date: Mar. 9, 2006

(65) Prior Publication Data
US 2008/0009810 A1     Jan. 10, 2008

(30) Foreign Application Priority Data
Aug. 28, 2004  (GB) .................................. 0419238.1

(51) Int. Cl.
*A61M 5/32* (2006.01)
(52) U.S. Cl. ................. 604/265; 604/21; 604/103.1
(58) Field of Classification Search .......... 600/380; 604/162, 265, 287
See application file for complete search history.

(56) References Cited

U.S. PATENT DOCUMENTS

| | | | |
|---|---|---|---|
| 3,951,136 A | 4/1976 | Wall | |
| 4,776,349 A | 10/1988 | Nashef et al. | |
| 5,109,870 A * | 5/1992 | Silny et al. | 600/593 |
| 5,179,952 A | 1/1993 | Buinevicius et al. | |
| 5,389,074 A | 2/1995 | Parker et al. | |
| 5,551,953 A * | 9/1996 | Lattin et al. | 604/20 |
| 5,762,638 A * | 6/1998 | Shikani et al. | 604/265 |
| 5,836,895 A * | 11/1998 | Ramsey, III | 600/593 |
| 6,148,222 A * | 11/2000 | Ramsey, III | 600/380 |
| 6,259,938 B1 * | 7/2001 | Zarychta et al. | 600/380 |
| 6,464,697 B1 * | 10/2002 | Edwards et al. | 606/41 |
| 6,484,053 B2 | 11/2002 | Leelamanit et al. | |
| 6,611,699 B2 * | 8/2003 | Messing | 600/372 |
| 6,613,025 B1 * | 9/2003 | Palasis | 604/265 |

(Continued)

FOREIGN PATENT DOCUMENTS

EP          0 510 857         10/1992

(Continued)

OTHER PUBLICATIONS

Jasper, Herbert H. (1958) "The Ten Twenty Electrode System of the International Federation," *Clinical Neurophysiol* 10: 370-375.

(Continued)

*Primary Examiner* — Kevin C Sirmons
*Assistant Examiner* — Brandy C Scott
(74) *Attorney, Agent, or Firm* — Morrison & Foerster LLP (57) ABSTRACT

A device for assisting recovery from dysphagia, and a method of preventing and/or treating dysphagia. The device includes a catheter suitable for insertion into the body of a patient, for the introduction of nutrients to the stomach of said patient, and electrodes located on a surface of the catheter, the electrodes being positioned such that when the catheter is inserted into a patient the electrodes are in a suitable position for applying electrical pharyngeal stimulation.

29 Claims, 5 Drawing Sheets

U.S. PATENT DOCUMENTS

| | | | |
|---|---|---|---|
| 6,658,294 | B1 | 12/2003 | Zadeh et al. |
| 6,856,822 | B2 * | 2/2005 | Larsson ................ 600/373 |
| 2003/0036794 | A1 | 2/2003 | Ragheb et al. |
| 2004/0034396 | A1 | 2/2004 | Freed et al. |
| 2004/0230162 | A1 * | 11/2004 | Tan ................ 604/171 |
| 2006/0085049 | A1 * | 4/2006 | Cory et al. ................ 607/48 |

FOREIGN PATENT DOCUMENTS

| | | |
|---|---|---|
| GB | 2-169-206 A | 7/1986 |
| GB | 2 254 253 | 10/1992 |
| GB | 2 294 642 | 5/1996 |
| JP | 63-200771 | 8/1988 |
| JP | 5-115563 | 5/1993 |
| JP | 7-500523 | 1/1995 |
| JP | 8-505291 | 6/1996 |
| JP | 10-118190 | 5/1998 |
| WO | WO-94/00050 | 1/1994 |
| WO | WO-94/05361 | 3/1994 |
| WO | WO 97/15349 A1 | 5/1997 |
| WO | WO-97/19667 | 6/1997 |

OTHER PUBLICATIONS

Wassermann Eric M. (1996) "Risk and safety of repetitive transcranial magnetic stimulation: report and suggested guidelines from the International Workshop on the Safety of Repetitive Transcranial Magnetic Stimulation" *Electroencephalography and clinical Neurophysiology 108*: 1-16.

Fraser, C. et al (2002). "Driving Plasticity in Human Adult Motor Cortex is Associated with Improved Motor Function after Brain Surgery," *Neuron* 34(5):831-840.

Gow, D. et al (2004). "Characterising the Central Mechanisms of Sensory Modulation in Human Swallowing Motor Cortex," *Clinical Neurophysiology* 115(10):2382-2390.

Hamdy, S. et al (1998). "Recovery of Swallowing After Dysphagic Stroke Relates to Functional Reorganization in the Intact Motor Cortex," *Gastroenternology* 115 (5):1104-1112.

Hamdy, S. et al (2003). "Modulation of Human Swallowing Behaviour by Thermal and Chemical Stimulation in Health and After Brain Surgery," *Neurogastroenterol Motil.* 15(1):69-77.

Kajii, Y. et al (2002). "Sour Taste Stimulation Facilitates Reflex Swallowing from the Pharynx and Larynx in the Rat," *Physiology & Behavior* 77(2-3):321-325.

Tutuian, R. et al (2003). "Effects of Position on Oesophageal Function: Studies Using Combined Manometry and Multichannel Intraluminal Impedance," *Neurogastroenterol Motil.* 15(1):63-67.

Takeuchi, H. et al (1994). "Electrophysiological and Behavioral Studies of Taste Discrimination in the Axolotl (*Ambystoma mexicanum*)," *Physiology & Behavior* 56(1):121-127.

International Search Report mailed on Dec. 30, 2005 for International Patent Application No. PCT/GB2005/003289. 8 pages.

Written Opinion of the International Searching Authority mailed on Dec. 30, 2005 for International Patent Application No. PCT/GB2005/003289. 8 pages.

Great Britain Search Report dated Nov. 1, 2004, directed to counterpart GB application No. 0419238.

\* cited by examiner

DYSPHAGIA RECOVERY BY ELECTRICAL STIMULATION

BACKGROUND

1. Field of the Invention

The present invention relates to a method and apparatus for facilitating recovery from dysphagia.

2. Description of the Related Art

Dysphagia is the condition whereby a patient has difficulty in swallowing, or is unable to swallow. Dysphagia may be caused, for example, by stroke, neurodegenerative diseases, brain tumours or in some case by other co-morbidity such as respiratory disorders.

Swallowing is a rigidly ordered sequence of events that results in the propulsion of food from the mouth through the pharynx and esophagus to the stomach. At the same time, respiration is inhibited and food is prevented from entering into the trachea. Swallowing can be initiated voluntarily, but thereafter it is almost entirely under reflex control. The swallowing reflex is typically initiated by sensory impulses from tactile receptors (particularly those located near the opening of the pharynx) being transmitted to certain areas in the medulla. The central integrating areas for swallowing lie in the medulla and lower pons; they are collectively called the swallowing centre. Motor impulses travel from the swallowing centre to the musculature of the pharynx and upper esophagus via various cranial nerves. This lower swallowing centre in the brainstem is under regulatory control by higher centres in the cerebral cortex. These higher swallowing centres or regions control the voluntary initiation and modulation of the swallow.

Swallowing occurs in three stages. In the oral or voluntary phase, food is moved towards the back of the mouth by the tongue, and forced into the pharynx, where it stimulates the tactile receptors that initiate the swallowing reflex.

In the pharyngeal stage of swallowing, food passes through the pharynx by constriction of the walls of the pharynx, backward bending of the epiglottis, and an upward and forward movement of the larynx and trachea. During the pharyngeal stage, respiration is reflexively inhibited.

In the esophageal stage of swallowing, food moves down the esophagus and into the stomach, assisted by one or more peristaltic waves.

Although the main function of swallowing is the propulsion of food from the mouth into the stomach, swallowing also serves as a protective reflex for the upper respiratory tract, preventing unwanted particles from entering the tract. For instance, dysphagia after a stroke can be a devastating problem, as it carries a six fold increased risk of aspiration pneumonia.

In the past, a number of separate treatments have been utilised to assist patients in regaining adequate swallowing reflexes.

For instance, some patients have undergone thermal stimulation treatment. In thermal stimulation treatment, the tonsillar fossa is stimulated by a cooled mirror or probe, and the patient closes his mouth and attempts to swallow.

Alternatively, international patent application no. PCT/US96/17015 describes a method for treating dysphagia with electrical stimulation. The application describes a non-invasive method for treating dysphagia and artificially promoting swallowing by electrical stimulus. A plurality of electrodes are selectively placed in electrical contact with skin over the neck, around the pharyngeal region of the patient, and a series of electrical pulses applied to the electrodes. The electrical pulses selectively stimulate muscle located proximate to the electrodes, to beneficially alter swallowing function. The patent application describes how patients treated by electrical stimulation recovered the ability to swallow at a faster rate than those patients treated by thermal stimulation.

BRIEF SUMMARY OF THE INVENTION

It is an aim of embodiments of the present invention to provide a therapeutic technique and an associated device that facilitates the process of recovery of patients from dysphagia. It is an aim of particular embodiments to provide a therapeutic technique and associated device that helps speed up the process of recovery.

In a first aspect, there is provided a device for assisting recovery from dysphagia, comprising a catheter suitable for insertion into the body of a patient, for the introduction of nutrients to the stomach of said patient, and electrodes located on a surface of the catheter, the electrodes being positioned such that when the catheter is inserted into a patient the electrodes are in a suitable position for applying electrical pharyngeal stimulation.

The device allows the provision of intraluminal electrical pharyngeal stimulation combined with the maintenance of nutrition and/or the delivery of chemicals or drugs to the patient via a feeding delivery system (a catheter), both of which will enhance the recovery process. Further, the proportion of patients recovering the ability to swallow, and/or the degree to which the swallowing ability is recovered, can be increased.

In a second aspect, there is provided a method of assisting recovery from dysphagia, comprising: applying electrical pulses capable of inducing pharyngeal stimulation to electrodes located on the surface of a catheter, the catheter being inserted into the body of a patient for the introduction of nutrients to the stomach of said patient, and the electrodes being located in a position suitable for applying electrical pharyngeal stimulation.

Preferably, the device further comprises a delivery unit for intra-luminal delivery into the patient of a stimulus in the form of an active agent capable of activating the swallowing stimulus.

Preferably, the catheter further comprises the chemical delivery unit, with the chemical delivery unit taking the form of an additional aperture on the catheter for the introduction of said active agent into the patient.

Preferably, the delivery unit comprises a dissolvable coating on at least a portion of a surface of the catheter.

Preferably, the device further comprises a moveable cover mounted on the catheter for control of the release of the active agent, the cover being arranged to move between a first position in which the coating is covered, and a second position in which the coating is at least partially exposed.

Preferably, the device further comprises a control unit arranged to generate an electrical signal, coupled to the delivery unit, the delivery unit being arranged to selectively release said active agent in response to the electrical signal.

Preferably, the active agent acts as a taste stimulus.

Preferably, said active agent comprises an aversive tasting substance.

Preferably, said active agent comprises a strong tasting substance.

Preferably, said active agent comprises quinine.

Preferably, said active agent comprises quinine hydrochloride.

Preferably, said active agent comprises citric acid.

Preferably, said active agent is arranged to promote the release of at least one type of endocrine hormone.

Preferably, said endocrine hormone comprises cholecystokinin.

Preferably, the device further comprises a catheter position indicator arranged to indicate when the catheter is located in a predetermined position within a patient.

Preferably, said catheter positioning unit comprises electrodes located on a surface of the catheter, and an impedance measuring unit for determining when said electrodes are in contact with pharyngeal mucosa of the patient.

Preferably, the catheter positioning unit comprises a pressure sensor mounted on the catheter, for measurement of the high pressure zone in the upper oesophagus sphincter of the patient.

Preferably, the device further comprises a stimulator arranged to apply transcranial magnetic stimulation.

Preferably, the device is arranged to apply a first of said stimuli continuously, and a second of said stimuli periodically.

Preferably, the device is arranged to apply the first stimulus periodically at a first frequency, and arranged to apply the second stimulus at a second frequency.

Preferably, said second frequency is equal to said first frequency, and the device is arranged to apply the second swallowing stimulus a predetermined interval after said first stimulus.

Preferably, said predetermined interval is substantially 100 ms.

Preferably, the method comprises the step of generating the electrical pulses.

Preferably, said electrical pulses are applied at a frequency within the range 0.5 Hertz to 5 Hertz.

Preferably, the electrical pulses have a peak amplitude in the range 1 mA to 50 mA.

Preferably, the method further comprises the step of inserting the catheter through the nose or mouth of a patient, into the patient for the introduction of nutrients to the stomach of said patient.

Preferably, the catheter further comprises a catheter position indicator, the catheter being inserted into the patient until the indicator indicates the catheter is located in a predetermined position within said patient.

Preferably, the catheter position indicator is a visible mark on an exterior surface of the catheter.

Preferably, the method further comprises delivering into the patient a stimulus in the form of an active agent capable of activating the swallowing reflex.

BRIEF DESCRIPTION OF THE DRAWINGS

Specific embodiments of the present invention will now be described, by way of example only, with reference to the accompanying drawings in which.

DETAILED DESCRIPTION OF THE INVENTION

The present invention relates to a device and associated method for assisting recovery from dysphagia, by providing different types of swallowing stimuli, either alone or in combination to a patient.

The patient can be a person or an animal. A swallowing stimulus is a stimulus that initiates, facilitates or improves the retention of the swallowing reflex. For instance, it is known that electrical stimulation of the neck region can be used to treat dysphagia, and allow a patient to recover the ability to swallow at a faster rate. Equally, more invasive intraluminal pharyngeal stimulation has been reported as being strongly correlated with an improvement in swallowing function (as reported in the article "Driving Plasticity in Human Adult Motor Cortex is associated with Improved Motor Function after Brain Injury" Neuron, Vol. 34, 831-840, May 30, 2002, by Chris Fraser, Maxine Power, Shaheen Hamdy et al.). The present inventor has realised that combining two or more types of swallowing stimuli can lead to a further improvement in swallowing function.

Figure 1:
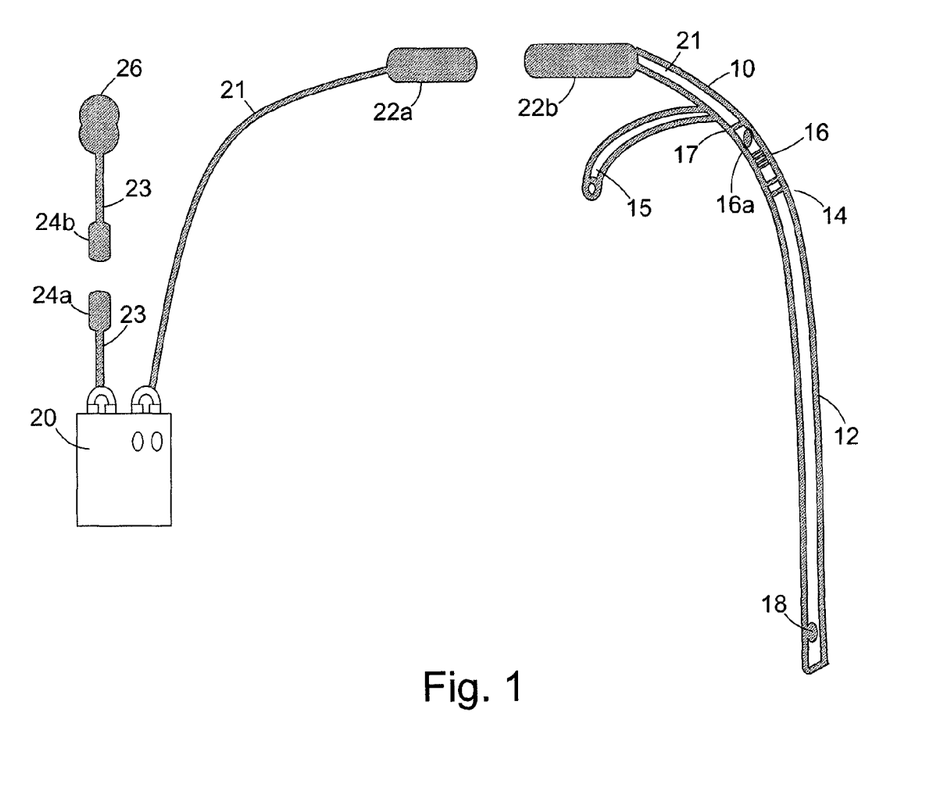
FIG. 1 illustrates a schematic diagram of a device for assisting recovery from dysphagia, in accordance with a preferred embodiment of the present invention.

FIG. 1 shows a device 10 in accordance with a preferred embodiment of the present invention, that is suitable for providing intraluminal electrical pharyngeal neuromuscular stimulation, which can be combined with transcranial magnetic stimulation (TMS), and taste stimulation. The device 10 is also arranged to provide the patient with nutrients.

The device 10 comprises a catheter 12. The catheter 12 is in the form of a longitudinally extending tube, for introducing nutrients into the stomach of the patient. The tube is suitably sized for insertion via at least one of the nose (e.g. via a nostril) and the mouth of the patient. The tube is long enough to pass through the nose or mouth, and via the pharynx and esophagus into the stomach.

The catheter 12 has a connector 15 arranged for connection to an infusion channel of a nutrient delivery system external to the patient. The other end of the catheter 12 has an aperture 18, for infusion of the nutrients into the stomach of the patient.

At least one pair of electrodes 14 is located on an external surface of the catheter 12. The electrodes 14 are positioned on the catheter at an appropriate position for providing intraluminal pharyngeal stimulation, when the catheter 12 has been inserted into a patient. The electrodes 14 are connected via a conductive cable 21 to an electrical signal generator 20. The electrical signal generator 20 is arranged to generate a series of electrical pulses, at a predetermined frequency, the pulses being of a predetermined duration, and of predetermined power or current, suitable for electrical stimulation of the intraluminal surface of the pharynx.

In a preferred embodiment, the electrical signal generator is arranged to produce pulses at a predetermined frequency in the range of 0.05 to 5 Hertz, each pulse being of duration 200 milliseconds. Preferably, the pulses have a current of between 1 and 50 milliamps. Preferably the pulses are delivered at a voltage of 280 millivolts. Preferably, the electrical signal generator is arranged to deliver a train of pulses for a predetermined period between 10 and 30 minutes.

The electrical signal generator 20 is preferably powered by a battery, rather than an external power supply. Preferably the generator 20 has the capacity to measure electrical impedance, so that the operator can check for "good" electrical contact between the electrodes and the pharyngeal mucosa, e.g. via a light indicator on the generator indicative of the measured impedance. The signal generator 20 is connected to the electrodes via mating connection sockets 22a, 22b disposed along the cable 21. Disconnection of the connection sockets 22a, 22b is used to decouple the signal generator 20 from the electrodes 14. This is advantageous when the catheter 12 is being inserted into the patient, as the less extraneous devices coupled to the catheter, the better, as such devices are likely to impede the freedom of movement of the catheter, or become entangled with an operator.

The device 10 includes a catheter position indicator 17, for indicating when the catheter is located in a predetermined position within the patient. In this particular embodiment, the catheter position indicated 17 takes the form of an external mark on an external surface of the catheter 12. The mark is located at a position along the length of the catheter 12, such that when the catheter 12 is inserted into the patient, the mark will indicate to an operator when the catheter has been inserted into the patient the desired distance. For instance, if the catheter is arranged to be inserted into the mouth of a patient, then the mark can be positioned along the length of the catheter 12 such that when the mark is aligned with the front teeth of the patient, then the catheter 12 is correctly positioned within the patient. Different sized catheters can be used for different builds, sexes and/or sizes of patient. Alternatively, the catheter may be cut to the appropriate size for any given patient, or a range of different marks provided on the catheter for different patients, the positions of the marks varying depending on whether the catheter is passed by mouth or through the nose.

The device 10 further comprises an electromagnet 26 and 27 coupled to the electrical signal generator 20 by electrical cable 23. The electromagnet 26 and 27 can be de-coupled from the electrical signal generator 20 by detaching connection sockets 24a, 24b disposed along the length of the cable 23. The electromagnet 26 is used to provide TMS 27. The electromagnets can take the form of a conducting coil connected to a capacitor. Alternatively, the electrical signal generator 20 can incorporate a magnetic stimulator (e.g. similar to the Magstim200, manufactured by MAGSTIM Company Ltd, Witland, Wales), with the magnet taking the form of a figure-of-8-coil. For instance, figure-of-8-coils of outer diameter 50 mm and 70 mm have been used in previous TMS trials. The maximum output of the 70 mm outer diameter figure-of-8-coil is typically 2.2 Tesla.

The device 10 further comprises at least one chemical delivery unit, arranged to deliver a chemical to the patient. In this particular instance, two chemical delivery units are located on the catheter. In this embodiment the first chemical delivery unit is a dissolvable coating 16. The coating 16 is arranged to dissolve when located within a pre-determined portion of the human body, and to release a predetermined chemical as it dissolves. The coating used here is arranged to dissolve when inserted into the mouth of a patient due to the action of saliva upon the coating. Consequently, the coating 16 is located along the length of the catheter 12, such that when the catheter 12 is inserted within the body of the patient, the coating will be positioned within the mouth of the patient. In this particular embodiment, the chemical that is released is arranged to act as a taste stimulus. The taste stimulus maybe quinine hydrochloride. Preferably, the taste stimulus is an aversive taste, and more preferably, the chemical comprises a sour or bitter substance (these being as rated as intense or extremely intense by a healthy individual).

The second chemical delivery unit takes the form of a conduit, coupled to the device, and arranged to deliver a chemical to the patient. In this embodiment, the second chemical delivery unit takes the form of a port 16a in the catheter, located around the portion of the catheter corresponding to the mouth/base of tongue location. The port 16a allows the input of chemicals to the catheter, with such chemicals subsequently entering the gastrointestinal tract of the patient via an outlet aperture from the catheter.

Figure 2:
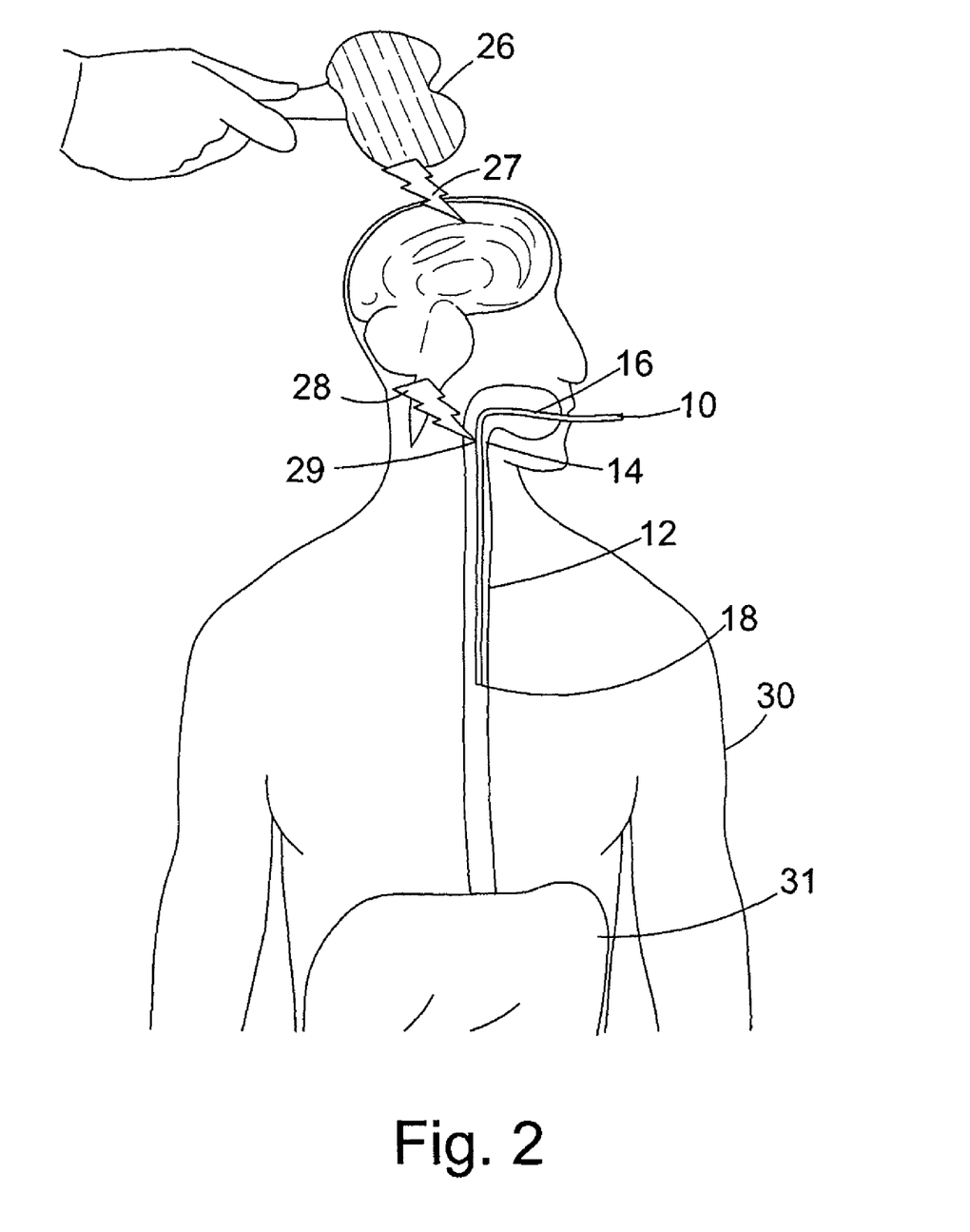
FIG. 2 is a schematic diagram showing the treatment of a patient using the device shown in FIG. 1.

The use of the device 10 will now be described, with reference to FIG. 2. The catheter 12 of the device is inserted via the nose or mouth of a patient 30, so as to allow the provision of nutrients into the stomach 31 of a patient. The catheter may extend into the stomach 31 of the patient, or alternatively the catheter may be arranged to extend only into the upper portion of the upper G.I. (Gastro Intestinal) tract. The G.I. tract is the entire digestive system running from the mouth to the anus. The upper G.I. tract is the portion of the G.I. tract between the mouth and the stomach. The catheter is inserted into the patient 30 until the mark 17 on the outer surface of the catheter 12 indicates the catheter is correctly located within the patient. In this position, the electrodes 14 will be in electrical contact with the pharyngeal musculature 29. Further, the port 18 will open into the upper G.I. tract, so as to allow the administration of nutrients into the stomach 31. Additionally, the dissolvable compound 16 will be in contact with the saliva of the patient's mouth.

The connector 15 is connected to a nutrient supply, so as to deliver nutrients to the patient at a predetermined rate. The electrical signal generator 20 is electrically coupled to electrodes 14. The magnet 26 is connected to signal generator 20 by connecting together connection sockets 24a, 24b. The dissolvable coating 16 of the chemical delivery unit will continuously administer the desired tasting chemical to the patient, as the coating dissolves. The catheter can be used to supply nutrients to the patient. At periodic, predetermined intervals, the patient will be treated with electrical pharyngeal stimulation 28 by the intra-luminal electrodes 14, and if necessary in combination with TMS 27 by the magnet 26. If only the pharyngeal stimulation component of the device is being used alone or in association with the taste stimuli then preferably the electrical pulses are applied at a frequency of 5 Hertz by the signal generator 20. Preferably, the patient undergoes 1-3 sessions per day, for a maximum of 2 weeks. Should the TMS component, 27 be combined with the electrical pharyngeal stimulation 28 by the intra-luminal electrodes 14, and the patient has dysphagia due to a stroke, then preferably TMS 27 is applied to the side of the brain of the patient unaffected by the stroke. Preferably, TMS pulses are applied at a frequency in the range of 0.05 to 5 Hertz. Preferably, the amplitude of the pulse is limited to 120% of the hand motor threshold. Preferably, the magnetic pulses are restricted to 100 pulses per session. Preferably, the patient undergoes 1-3 sessions per day, for a maximum of 2 weeks. Preferably, the signal generator 20 is arranged to apply a magnetic pulse at a predetermined interval after a corresponding electrical pulse used in the electrical pharyngeal stimulation. Preferably, the predetermined interval is greater than 75 milliseconds, and more preferably it is approximately 100 milliseconds, or within the range 80-120 milliseconds. Preferably, the electrical pulses are applied at the same frequency as the TMS pulses.

Even more preferably, the patient undergoes one session of pharyngeal stimulation per day. Preferably, the patient undergoes a treatment of fifteen or less sessions of pharyngeal stimulation, more preferably five or less sessions of pharyngeal stimulation, and most preferably three sessions of pharyngeal stimulation. For example, in a preferred embodiment, the patient undergoes one session of electrical pharyngeal stimulation once a day, for three days.

Figure 3:
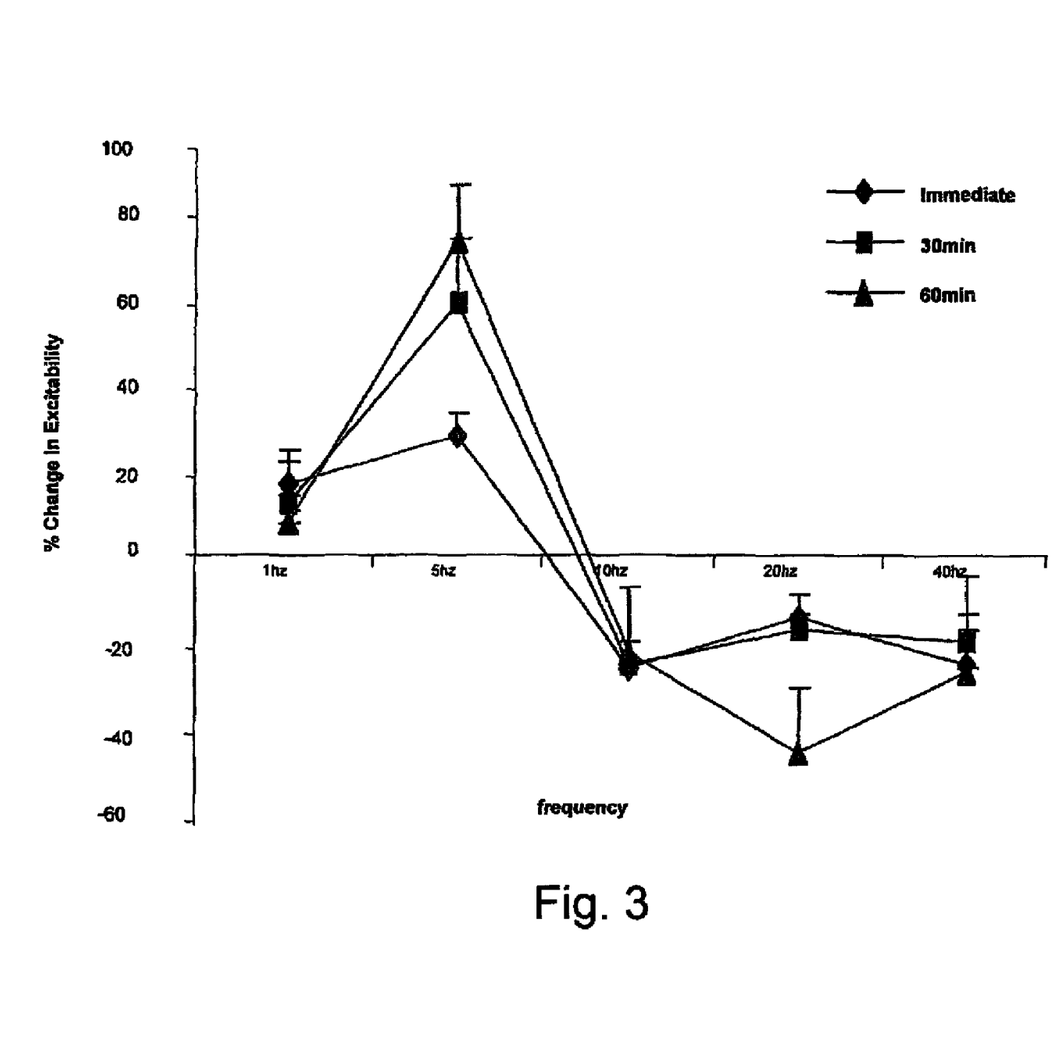
FIG. 3 is a graph indicating the change in pharyngeal cortical excitability following differing frequencies of intraluminal pharyngeal electrical stimulation for 10 minutes at 75% of the maximum tolerated intensity in accordance with an embodiment of the present invention.

FIG. 3 illustrates the change in pharyngeal cortical excitability for different frequencies or pulses utilised in electrical pharyngeal stimulation. FIG. 3 illustrates the change in cortical excitability immediately after the application of the pulse series, 30 minutes after the application of the pulse series, and 60 minutes after the application of the pulse series. The change in cortical excitability is determined by measuring the pharyngeal electromyographic trace for cortical stimulation prior to the application of the electrical pharyngeal stimulation, and also after (ie immediately, 30 minutes and 60 minutes after) the application of electrical pharyngeal stimulation. The percentage change in the excitability is the change in the pharyngeal electromyographic traces (ie the increase in the EMG traces due to pharyngeal stimulation), plotted as a percentage variation compared with the pre-pharyngeal stimulation traces for each patient.

FIG. 3 illustrates that the greatest percentage change in cortical excitability is exhibited by electrical pharyngeal stimulation applied using pulses at 5 Hertz.

It will be appreciated that the above embodiment is described by way of example only, and that various other embodiments will fall within the scope of the invention.

For instance, whilst the chemical delivery unit in the above embodiment is described as being arranged to deliver taste stimuli, it will be appreciated that the delivery unit can be used to provide any desired chemical stimulus ie any active agent capable of activating the swallowing stimulus. For instance, it can be used to provide a chemical stimulus to induce the release of the endocrine hormones, such as cholecystokinin (CCK), which are known to be linked to feeding behaviour. The chemical delivery units can thus be arranged to deliver chemical into any preferred portion of the anatomy including directly into the stomach via the nutrient delivery system already incorporated in to the catheter or via an additional port on the catheter situated in the mouth or throat region.

In the above embodiment, the chemical delivery unit has been described as providing a continuous supply of chemical, as the dissolvable coating dissolves. However, it will be appreciated that the dissolvable coating may be applied in layers, such that the chemical delivery unit intermittently supplies a particular chemical stimulus.

Alternatively, the chemical delivery unit can take the form of a dissolvable coating with a removable cover. For instance, a cover may be arranged to slide along the length of the catheter, to move between a first position in which it occludes the coating, and a second position in which the coating is exposed. By movement of the cover, the chemical delivery unit can be switched between a state in which it delivers the desired chemical and a state in which it substantially does not deliver the desired chemical.

Alternatively, rather than a dissolvable coating, the chemical delivery unit can take any other form suitable for delivering a chemical. For instance, it could take the form of one or more orifices within the catheter, with chemical being infused through the orifices into the patient, particularly the mouth, more particularly the tongue, and most particularly the rear of the tongue. Control of the chemical delivery unit can be via an electrical device arranged to switch the chemical delivery unit between a first state in which it provides the chemical to the patient, and a second state in which it does not.

In the above embodiment, the catheter position indicator is a mark upon a surface of the catheter. However, other catheter position indicators can be utilised. For instance, the catheter might comprise an impedance measurement device, arranged to measure the impedance between two electrodes positioned on an outer surface of the device. These impedance measuring electrodes could be positioned in proximity to the electrodes 14 for pharyngeal stimulation. Such a catheter 12 could be inserted into the patient until the impedance measured between the electrodes indicates that the electrodes are in contact with pharyngeal mucosa.

Alternatively, the catheter position indicator might take the form of a pressure sensor located along the length of the catheter. It is known that a relatively high pressure zone exists beyond the upper esophagus sphincter. The catheter could be inserted until the pressure sensor indicates an appropriate portion of the catheter is within the high pressure zone.

In the above embodiment, the catheter is described as being suitable to deliver nutrients into the stomach. The catheter can however be arranged to deliver nutrients directly into any portion of the upper gastrointestinal tract. Alternatively, the catheter can be utilised to act as one or more of the stimulator devices (e.g. the chemical delivery unit or the electrical pharyngeal stimulator).

Suitable stimuli for use as first and second swallowing stimuli in accordance with the invention may be selected from the group comprising electrical pharyngeal stimulation, stimulation of the cortex associated with swallowing, temperature stimulation and chemical stimulation. Temperature stimulation encompasses the use of either raised or lowered temperature as a stimulus. Transcranial magnetic stimulation provides a suitable method by which areas of the cortex associated with swallowing may be stimulated.

Either the first or second types of swallowing stimuli may be central or peripheral swallowing stimuli. Thus the swallowing stimuli may comprise first and second peripheral stimuli, or first and second central stimuli. Preferably, however, the first and second swallowing stimuli comprise a peripheral stimulus and a central stimulus. Suitable peripheral and central stimuli may be selected from the group of stimuli considered above and applied in isolation or in combination.

A chemical swallowing stimulus suitable for use in accordance with the invention may, for instance, comprise a taste stimulus. Such a taste stimulus may comprise any of the four basic tastes recognised by the mouth (for the present purposes sweet, sour, salt and bitter) or any combination thereof. The inventors have surprisingly found that aversive tastes are of particular utility in promoting a swallowing response, and accordingly the taste stimulus may preferably be an aversive stimulus such as a chemical stimulus having a bitter or sour or associated strongly flavoured taste.

A chemical swallowing stimulus, and particularly a taste stimulus, may advantageously be administered to the mouth of a patient. More particularly the chemical swallowing stimulus may be administered to the surface of the tongue, and preferably to the rear of the tongue.

A suitable chemical stimulus may even be one that increases the activity of an endocrine hormone associated with feeding behaviour. For example, the chemical stimulus may be one that increases the activity of cholecystokinin. It will be appreciated that suitable chemicals stimuli may include the endocrine hormone itself, biological precursors of the endocrine hormone, and agents capable of causing an increase in the release or synthesis of the endocrine hormone. In the case that the chemical swallowing stimulus comprises an endocrine hormone, or a biological precursor thereof, it may be preferred that the endocrine hormone be administered to an anatomical site at which it has its biological effect. It will be appreciated endocrine hormones achieving their effect in the upper portions of the gastrointestinal tract may be administered to a suitable location by means of the catheter of a device of the type described above.

Example 1

This example illustrates the effects of IPAS (Interventional Paired Associative Stimulation) at three different inter-stimulus intervals (ISI's) on the cortical excitability of swallowing musculature. IPAS relates to the pairing of peripheral and central stimuli, and has been previously illustrated as a novel method of enhancing hand cortical excitability. However, the development of dysphagia post stroke, and it's subsequent recovery, has been associated with changes in the excitability of the swallowing motor cortex, as for instance described within the article "Recovery of swallowing after dysphagic stroke relates to functional reorganization in the intact motor cortex. Gastroenterology 115: 1104-1112, 1998 by Shaheen Hamdy et al.

In the present experiment, 8 healthy human subjects were stimulated using paired stimuli. Each subject sat comfortably in a reclining chair, the cranial vertex was identified according to the international 10-20-system for electrode placement (The 10-20 electrode system of the International Federation. Electroenceph. Clin. Neurophysiol. 1958; 10: 371-375 by H. H. Jasper) and marked on the scalp and the pharyngeal catheter inserted trans-orally or trans-nasally (depending on subject preference).

Single pulse (monophasic) transcranial stimulation (sTMS) of the cerebral cortex was achieved using a magnetic stimulator (a Magstim 200, manufactured by MAGSTIM Company Limited, Whitland, Wales) connected to a 70 mm outer diameter figure-of-8 coil (maximal output of 2.2 Tesla (T)), held in an A-P (Anterior-Posterior) direction, at an angle of 45° tangential to the scalp.

Repetitive (biphasic) transcranial magnetic stimulation (rTMS) of the cerebral cortex was achieved using a Magstim Super Rapid stimulator (manufactured by MAGSTIM Company Limited, Whitland, Wales) connected to a 70 mm outer diameter figure-of-8 coil (maximal output of 1.8 Tesla (T)), held in an identical orientation to sTMS.

EMG (electromyographic) responses were recorded from the pharynx. Pharyngeal MEPs (motor evoked potentials) were recorded using a pair of bipolar platinum ring electrodes built into a 3 mm diameter intraluminal catheter (manufactured by Gaeltec, Dunvegan, Scotland) that was swallowed and positioned in the oropharynx. Response signals were passed through a pre-amplifier (a CED 1902, manufactured by Cambridge Electronic Design, Cambridge, England, UK) with filter settings of 5 Hz-2 kHz and collected through a laboratory interface (CED 1401 plus) at a sampling rate of 4-8 kHz. Data were displayed on a 486 PC.

Electrical stimulation of the pharynx was performed using a pair of bipolar platinum ring electrodes built into a swallowed 3 mm diameter intraluminal catheter (manufactured by Gaeltec, Dunvegan, Scotland) connected to an electrical stimulator (Model DS7; manufactured by Digitimer, Welwyn-Garden City, Herts, UK) via a trigger generator (DG2, manufactured by Digitimer), which delivered stimuli (ie pulses of pulse width 0.2 ms, amplitude 280V) at a predetermined intensity (current) and duration (see below). This stimulating electrode was positioned 1 cm distal to the recording electrode (see below) to minimise stimulus artefact.

The pharyngeal electrical stimulation intensity was determined in the following way; sensory threshold was calculated as the average of three trials comprising the first reported perceptible sensation to pharyngeal electrical stimulation with stepwise increments of 0.1 mA from zero stimulator output. Maximum tolerated intensity was calculated in a similar manner but this time the subject was asked to withstand the increments for as long as possible. These values were defined as perception and maximum tolerated intensities respectively. The active intensity of stimulation was then set at 75% of the difference between the perception and the maximum tolerated intensities.

Next, the sTMS "figure-of-eight" coil was discharged over both motor cortices, using 100% of stimulator output and the hemisphere evoking the greatest pharyngeal MEP amplitude was identified. The site over this hemisphere producing the largest pharyngeal responses was then identified and marked on the scalp. This site was stimulated using sTMS, commencing at subthreshold intensity and increasing by 5% steps until an intensity (to the nearest 5%) was found that evoked an MEP in the pharynx greater than 20 μV on at least 5 of 10 consecutive stimulations. This was defined as the motor threshold (MT) for the pharynx. Surface electrodes were then placed over the contralateral thenar eminence and the optimal site for evoking the greatest thenar MEP response was marked on the scalp. The thenar MT was then identified as the stimulation intensity producing MEP responses of 100 μV on at least 5 out of 10 consecutive stimulations.

To assess pre-stimulation swallowing motor cortex excitability, the pharyngeal site was then stimulated in a randomised order at intensities of 95%, 100%, 105%, 110%, 115%, and 120% of motor threshold using sTMS with 5 stimuli being performed at each intensity. To avoid any inadvertent facilitation of the cortically evoked responses, all subjects kept as relaxed as possible and minimised swallowing, coughing or speaking during the study (Hamdy et al., 1996). If any of these activities did inadvertently occur during the recording of an evoked response, that response was discarded and the stimulus repeated. Next, the stimulation intensity for rTMS was determined with the rTMS system in single pulse mode and set at 80% of pharyngeal motor threshold but capped at 120% of the thenar motor threshold to comply with standard safety recommendations (Risk and safety of repetitive transcranial magnetic stimulation: report and suggested guidelines from the International Workshop on the Safety of Repetitive Transcranial Magnetic Stimulation, Jun. 5-7, 1996. Electroencephalogr. Clin. Neurophysiol. 1998; 108; 1-16 by E. M. Wassermann).

Combined pharyngeal electrical and cortical magnetic stimuli (or IPAS) were applied for 30 minutes to each patient, using paired stimuli every 20 seconds, with firstly the electrical pharyngeal stimulus being applied, and subsequently the cortical stimulus to the swallowing motor area. Inter stimulus intervals of 50, 75 and 100 milliseconds were randomly tested on separate visits.

Pharyngeal excitability was then assessed immediately post IPAS using sTMS at intensities of 95%, 100%, 105%, 110%, 115%, and 120% of motor threshold, with 5 stimuli being performed at each intensity, the order of stimulus delivery being randomised. Assessments of excitability were repeated at 30, 60, 90 and 120 minutes.

Figure 4:
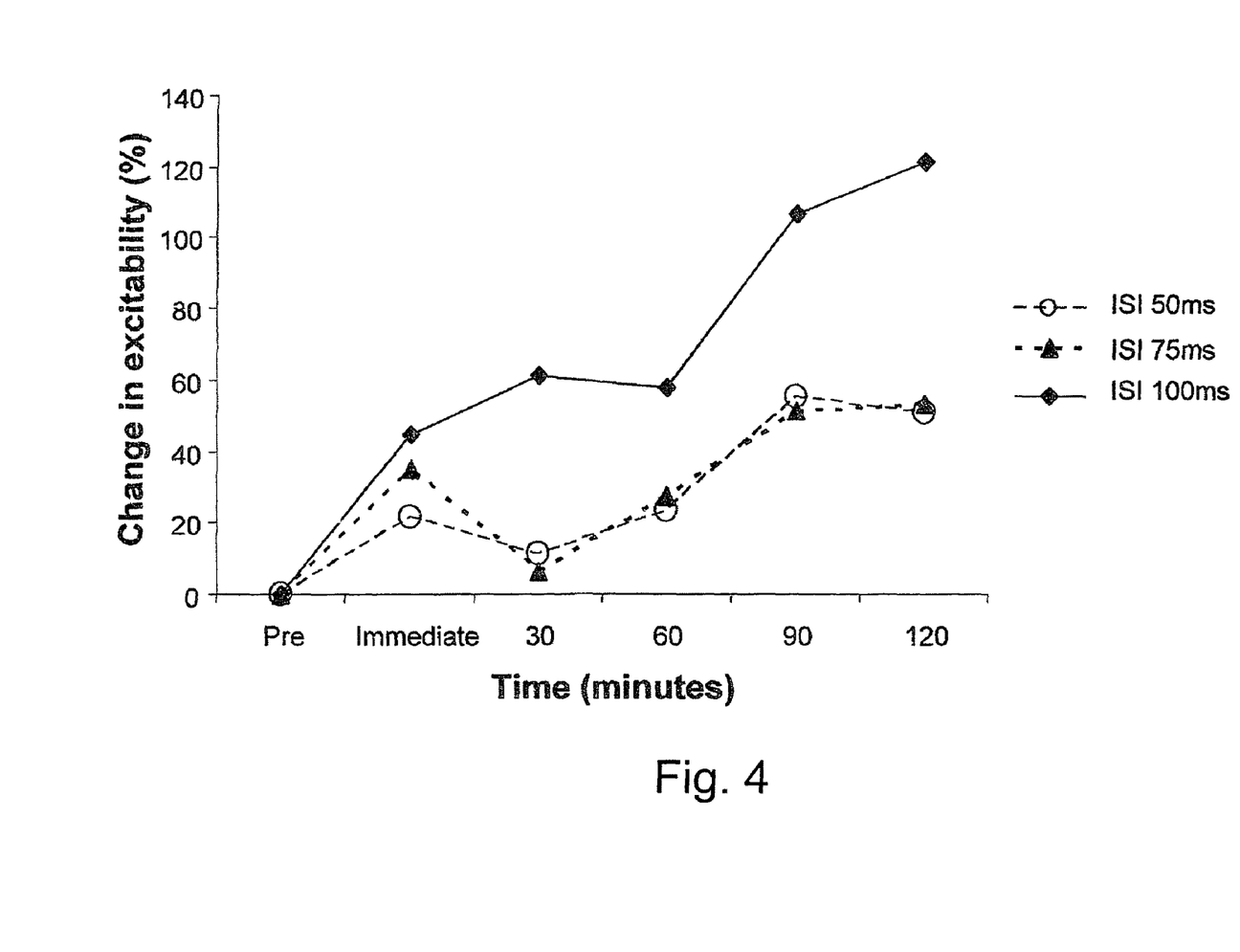
FIG. 4 is a graph indicating the change in pharyngeal cortical excitability following interventional paired associative stimulation (IPAS) in accordance with an embodiment of the present invention.

FIG. 4 illustrates the change in pharyngeal EMG following IPAS. The different ISI time periods (50, 75 and 100 milliseconds) are indicated. It can be seen that an ISI of 100 milliseconds shows the greatest change in cortical excitability (120% increase), which was sustained to two hours.

Example 2

An assessment was made on the effects of different taste experiences on human cortical swallowing pathways. The assessment was made upon 8 healthy adult volunteers (seven of which were male, the minimum age of the volunteers being 29 years).

Each volunteer performed a ten-minute, liquid swallowing task using three (previously titrated) different taste solutions. The three solutions utilised were sterile water (neutral taste), 10% glucose (sweet/pleasant taste), and 0.5 mM quinine hydrochloride (bitter/aversive taste). Solutions were randomised to separate studies at least 24 hours apart.

Transcranial magnetic stimulation was performed over the swallowing motor cortex, before and up to one hour after each swallow task as with the methodology described in example 1. Cortico-pharyngeal motor responses were recorded from a swallowed intra-luminal catheter as a measure of cortical excitability. Responses were then compared using repeated measures ANOVA (Analysis of Variance).

Figure 5:
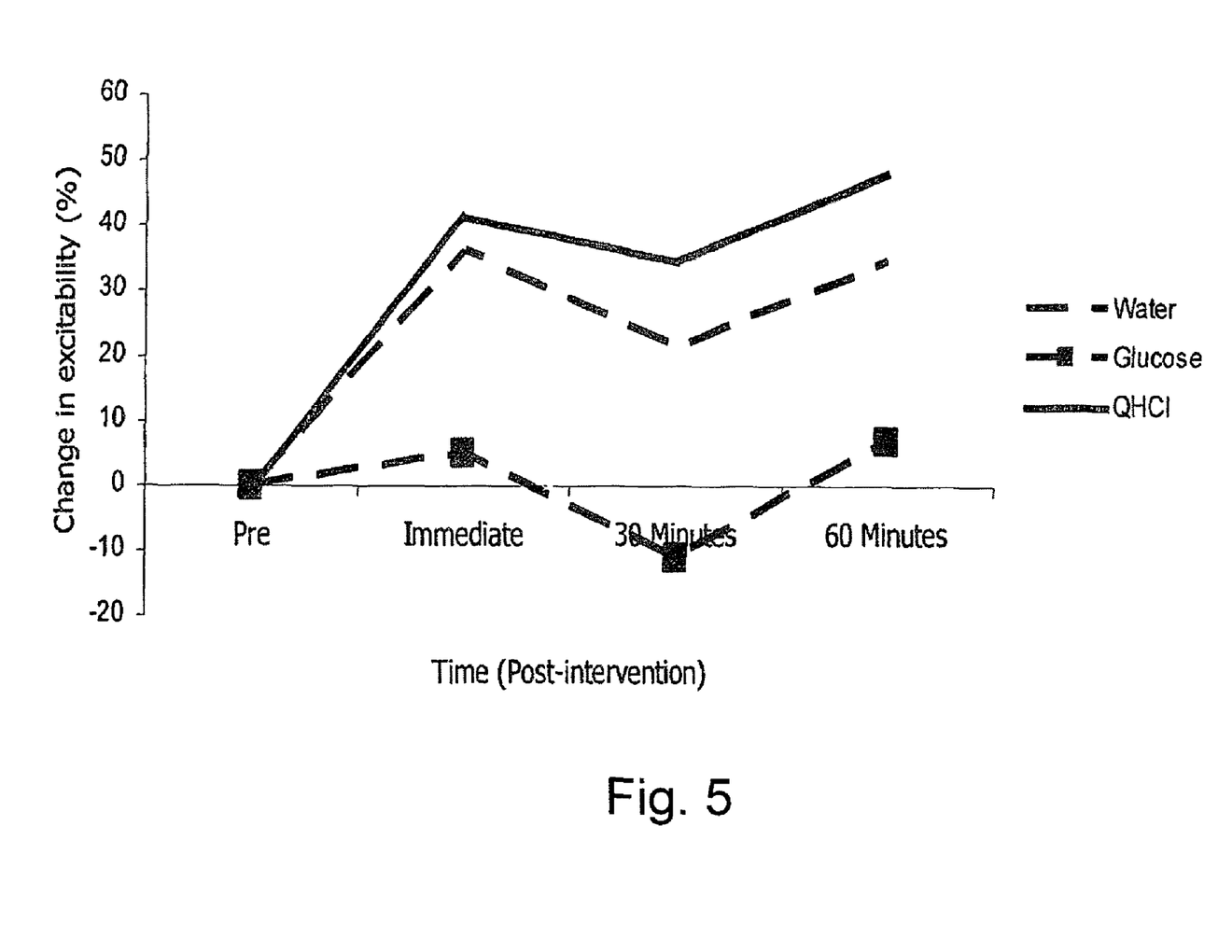
FIG. 5 is a graph indicating the change in pharyngeal cortical excitability with time, following the application of three different tasting stimuli.

FIG. 5 shows the percentage change in pharyngeal MEP amplitude from the base line MEP measurement at different time intervals prior to and after the swallowing task had been completed. It can be seen that cortico-pharyngeal responses for neutral water were increased, but only in the period immediately after swallowing (percentage change from baseline equals 36±15%, p<0.04, where p is the level of significance and taken to be relevant at <0.05). At 30 minutes, whilst still raised, the water effect was no longer significant. Following the glucose swallowing task, no substantial changes in response are observed.

However, following the quinine task, patients exhibited response that were increased compared to those exhibited following the water task, both immediately and throughout the 60 minutes post-intervention period (maximum percentage change from base line equals 48±11%, p<0.01).

It thus appears that cortical swallowing pathways are modulated in a differential manner by pleasant and aversive tasting stimuli. In comparison to neutral stimuli, aversive tastes are more enhancive to the cortical swallowing responses, whereas pleasant tastes may suppress these pathways. On this basis, it would appear that taste stimuli (particularly bitter or aversive taste stimuli) can be utilised as method for rehabilitating swallowing problems after cerebral injury.

The exact mechanism by which the cortico-pharyngeal responses were increased by quinine may be due to additional factors, other than taste. For instance, it may be that quinine provides a chemical stimulation directly to the gut. For instance, it may be that the application of quinine is linked to the release of endocrine hormones such as CCK from the upper GI tract, a release of which is linked to feeding behaviour. On this basis, it may be preferable to release quinine at other locations within the body other than the mouth, or even to release endocrine hormones (or other stimulators of such hormones) into the body with nutrients such as C12 fatty acids (ie fatty acids with chains consisting of 12 carbon atoms) or other fat based solutions.

The invention claimed is:

1. A therapeutic device for assisting recovery from dysphagia by treatment at periodic predetermined intervals with electrical pharyngeal stimulation to stimulate the swallow centers, comprising:
    a catheter suitable for insertion into the body of a patient through the nose or mouth, including a tube having an aperture located proximate to a distal end for the introduction of nutrients to the stomach of said patient;
    a single pair of electrodes located on a surface of the catheter, the electrodes being located on the device such that when the catheter is inserted into a patient through the nose or mouth, and the distal end of the catheter is positioned in the stomach of the patient, the electrodes are in a suitable position for applying electrical pharyngeal stimulation to an intra-luminal surface of the patient's pharynx,
    an impedance measuring unit for determining when said electrodes are in good electrical contact with, and suitable for applying electrical pharyngeal stimulation to, the intra-luminal surface of the patient's pharynx, and
    an indicator in the form of a visible marker configured to provide an operator with confirmation that the single pair of electrodes is in a suitable position in respect to the intra-luminal surface of the patient's pharynx prior to applying electrical pharyngeal stimulation.

2. A device as claimed in claim 1, wherein the device further comprises a delivery unit for intra-luminal delivery into the patient of a stimulus in the form of an active agent capable of activating the swallowing stimulus.

3. A device as claimed in claim 2, wherein the catheter further comprises the chemical delivery unit, with the chemical delivery unit taking the form of an additional aperture on the catheter for the introduction of said active agent into the patient.

4. A device as claimed in claim 2, wherein the delivery unit comprises a dissolvable coating on at least a portion of a surface of the catheter.

5. A device as claimed in claim 4, wherein the device further comprises a moveable cover mounted on the catheter for control of the release of the active agent, the cover being arranged to move between a first position in which the coating is covered, and a second position in which the coating is at least partially exposed.

6. A device as claimed in claim 4, wherein the device further comprises a control unit arranged to generate an electrical signal, coupled to the delivery unit;
    the delivery unit being arranged to selectively release said active agent in response to the electrical signal.

7. A device as claimed in claim 2, wherein said active agent comprises an aversive tasting substance.

8. A device as claimed in claim 2, wherein said active agent comprises a strong tasting substance.

9. A device as claimed in claim 2, wherein said active agent comprises quinine.

10. A device as claimed in claim 9, wherein said active agent comprises quinine hydrochloride.

11. A device as claimed in claim 2, wherein said active agent comprises citric acid.

12. A device as claimed in claim 2, wherein said active agent is arranged to promote the release of at least one type of endocrine hormone.

13. A device as claimed in claim 12, wherein said endocrine hormone comprises cholecystokinin.

14. A device as claimed claim 1, further comprising a catheter position indicator arranged to indicate when the catheter is located in a predetermined position within a patient in which the electrodes are in contact with pharyngeal mucosa.

15. A device as claimed in claim 14, wherein the catheter positioning unit comprises a pressure sensor mounted on the catheter, for measurement of the high pressure zone in the upper esophagus sphincter of the patient.

16. A device as claimed in claim 1, further comprising a stimulator arranged to apply transcranial magnetic stimulation.

17. A device as claimed in claim 16, wherein the device is arranged to apply a first of said stimuli continuously, and a second of said stimuli periodically.

18. A device as claimed in claim 17, wherein the device is arranged to apply the first stimulus periodically at a first frequency, and arranged to apply the second stimulus at a second frequency.

19. A device as claimed in claim 18, wherein said second frequency is equal to said first frequency, and the device is arranged to apply the second swallowing stimulus a predetermined interval after said first stimulus.

20. A device as claimed in claim 19, wherein said predetermined interval is substantially 100 ms.

21. A method of assisting recovery from dysphagia, comprising:
  inserting a catheter through the nose or mouth of a patient, the catheter comprising an aperture located proximate to a distal end for introducing nutrients into the stomach of said patient, and a catheter position indicator, itself comprising a physical mark on an external surface of the catheter, to indicate that the catheter is located in a predetermined position within said patient wherein the electrodes are in contact with pharyngeal mucosa and the distal end of the catheter is in the patient's stomach,
  applying electrical pulses capable of inducing pharyngeal stimulation to a single pair of electrodes located on the surface of the catheter, the electrodes being located in a position suitable for applying electrical pharyngeal stimulation while the distal end of the catheter is in the patient's stomach,
  using an impedance measuring device to determine when the electrodes are in physical contact with the patient's pharyngeal mucosa, and
  confirming that there is desired contact between the electrodes and the intra-luminal surface of the patient's pharynx prior to applying electrical pharyngeal stimulation.

22. A method as claimed in claim 21, further comprising the step of generating the electrical pulses.

23. A method as claimed in claim 21, wherein said electrical pulses are applied at a frequency within the range 0.5 Hertz to 5 Hertz.

24. A method as claimed in claim 21, wherein the electrical pulses have a peak amplitude in the range 1 mA to 50 mA.

25. A method as claimed in claim 21, wherein, the method further comprises delivering into the patient a stimulus in the form of an active agent capable of activating the swallowing reflex.

26. A method as claimed in claim 21, wherein the method further comprises using an impedance measuring unit of the device to measure impedance between a set of impedance measuring contacts in order to obtain an indication that the electrodes are in contact with pharyngeal mucosa during treatment.

27. A device as claimed in claim 1, further comprising a set of impedance measuring contacts, wherein the impedance measuring unit measures the impedance between the impedance measuring contacts to determine when the electrodes are in contact with the intra-luminal surface of the patient's pharynx.

28. The device as claimed in claim 1, wherein the indicator comprises a light indicator.

29. The device of claim 1, wherein the electrodes consist of a pair of bi-polar electrodes.

* * * * *